United States Patent
Amin et al.

(10) Patent No.: US 9,279,765 B2
(45) Date of Patent: Mar. 8, 2016

(54) DYNAMIC LIGHT SCATTERING BASED MICRORHEOLOGY OF COMPLEX FLUIDS WITH IMPROVED SINGLE-SCATTERING MODE DETECTION

(75) Inventors: Samiul Amin, Bromborough (GB); Carlos Alberto Rega, Worcestershire (GB)

(73) Assignee: Malvern Instruments, Ltd., Malvern (GB)

(*) Notice: Subject to any disclaimer, the term of this patent is extended or adjusted under 35 U.S.C. 154(b) by 0 days.

(21) Appl. No.: 13/390,915

(22) PCT Filed: Aug. 17, 2010

(86) PCT No.: PCT/GB2010/051354
§ 371 (c)(1),
(2), (4) Date: Sep. 13, 2012

(87) PCT Pub. No.: WO2011/021032
PCT Pub. Date: Feb. 24, 2011

(65) Prior Publication Data
US 2013/0003061 A1    Jan. 3, 2013

Related U.S. Application Data

(60) Provisional application No. 61/274,480, filed on Aug. 17, 2009.

(51) Int. Cl.
*G01N 21/00* (2006.01)
*G01N 21/51* (2006.01)
(Continued)

(52) U.S. Cl.
CPC ........ *G01N 21/51* (2013.01); *G01N 2021/0346* (2013.01); *G01N 2021/4709* (2013.01); *G01N 2021/513* (2013.01)

(58) Field of Classification Search
CPC .............. G01N 21/55; G01N 21/4795; G01N 21/1717; G01N 11/04; G01N 2021/1787; G01N 2500/10; G01N 33/5029; G01N 21/49; G01N 33/5008; G01N 2011/008; G01N 21/4738; G01N 33/4905; G01N 11/02; G01N 2021/0346

USPC .................................................. 356/336–342
See application file for complete search history.

(56) References Cited

U.S. PATENT DOCUMENTS 6,016,195 A    1/2000  Peters
6,519,032 B1   2/2003  Kuebler
(Continued)

FOREIGN PATENT DOCUMENTS

CN    1821727      8/2006
JP    2002501622   1/2002
(Continued)

OTHER PUBLICATIONS

Rheolaser Lab, Micro-rheology for soft materials, brochure, Aug. 13, 2009.
(Continued)

*Primary Examiner* — Michael P Stafira
(74) *Attorney, Agent, or Firm* — Kristofer E. Elbing

(57) ABSTRACT

A fluid characterization measuring instrument comprises a sample vessel (14) for a bulk complex sample fluid having a capacity that is substantially larger than a domain size of the complex sample fluid and that is sufficiently large to cause bulk scattering effects to substantially exceed surface effects for the complex fluid sample, a coherent light source (12) positioned to illuminate the bulk complex sample fluid in the sample vessel and a first fibre (16) having a first end positioned to receive backscattered light from the sample after it has interacted with the sample. The first fibre is positioned close enough to an optical axis of the coherent light source and to the sample vessel to substantially decrease a contribution of multiply scattered light in the backscattered light. The instrument further comprises a first photon-counting detector (20) positioned to receive the backscattered light from a second end of the fibre, correlation logic (22) responsive to the first photon-counting detector and single-scattering fluid property analysis logic responsive to the correlation logic and operative to derive at least one fluid property for the sample fluid.

26 Claims, 3 Drawing Sheets

(51) Int. Cl.
*G01N 21/03* (2006.01)
*G01N 21/47* (2006.01)

(56) References Cited

U.S. PATENT DOCUMENTS

| | | | |
|---|---|---|---|
| 6,707,556 B2 * | 3/2004 | Turner et al. | 356/436 |
| 6,958,816 B1 | 10/2005 | Dogariu | |
| 7,318,336 B2 | 1/2008 | Roth | |
| 2009/0251696 A1 * | 10/2009 | McNeil-Watson et al. | 356/336 |

FOREIGN PATENT DOCUMENTS

| | | |
|---|---|---|
| JP | 2003065930 | 3/2003 |
| JP | 2008175723 | 7/2008 |
| WO | WO2009059008 | 5/2009 |
| WO | WO2009090562 | 7/2009 |

OTHER PUBLICATIONS

M.L. Gardel, M.T. Valentine and D.A. Weitz; "Microrheology"; Department of Physics and Division of Engineering and Applied Sciences, Harvard University, Cambridge MA 02138, pp. 1-53, 2005.
Ansari et al., Dynamic Light Scattering Particle Size Measurements in Turbid Media, Proceedings of the International Society for Optical Engineering (SPIE), pp. 146-156, vol. 3251, Jan. 27, 1998.
Liu et al., "Design of Optical Fiber Probe to Measure the Parameters of Hemorheology", Chine Medical Equipment 2008, vol. 23, issue 2, p. 8. Machine translation.
Li Xiao-na et, "Research Progress in Experimental Techniques and Its Relevant Theories of Cell Mechanics on Cytokinesis", Space Medicine and Medical Engineering 22(2):148. Machine translation.
Chinese Office Action issued Feb. 7, 2014. Cites Foreign Patent Document 2 and Non-Patent Literature Document 1.
Chinese Office Action issued Sep. 17, 2014. Cites Chinese equivalent of US Patent Document 1, Foreign Patent Document 1, and Non-Patent Literature Document 2.

* cited by examiner

DYNAMIC LIGHT SCATTERING BASED MICRORHEOLOGY OF COMPLEX FLUIDS WITH IMPROVED SINGLE-SCATTERING MODE DETECTION

FIELD OF THE INVENTION

This invention relates to methods and apparatus for obtaining the viscoelastic parameters of complex fluids, such as colloidal and biological complex fluids.

BACKGROUND OF THE INVENTION

Viscoelasticity means the simultaneous existence of viscous and elastic properties in a material. Many complex and structured fluids exhibit viscoelastic characteristics, i.e., they have the ability to both store energy like an elastic solid as well as dissipate energy such as a viscous liquid. When a stress is applied to such a viscoelastic fluid it stores some of the energy input, instead of dissipating all of it as heat and it may recover part of its deformation when the stress is removed.

The elastic modulus or G' represents storage of elastic energy, while the loss modulus G" represents the viscous dissipation of that energy. The magnitude of G' and G" for most complex fluids depends upon the time scales or frequency at which the property is probed. Depending upon the stress relaxation mechanisms present in the complex fluids, they may exhibit different behaviour (either G'>G" or G">G' or G'=G") at different frequencies. Having the ability to probe the viscoelastic response over a wide frequency range therefore provides insights into the stress-relaxation mechanisms in complex fluids, and since this is connected to the underlying structure of the complex fluid, insights into the underlying structure can be obtained.

Currently, high end rotational rheometers are used to measure these viscoelastic properties, but the measurement time can be quite long depending upon the frequency being probed. Also, a considerable amount of time can be spent in cleaning the rheometer's stage and preparing the test before the next sample can be loaded, making high-throughput measurements quite challenging. Other disadvantages of rotational rheometers include that they provide access to a very limited frequency range, and they require large sample volumes, typically greater than 1 ml.

Optical-based Microrheological techniques have also been used to measure viscoelastic properties of complex fluids. These involve embedding probe particles into a viscoelastic fluid of interest (polymer solution, surfactant solution etc.) and following the thermal motion of the probe particles. The thermally driven random motion of colloidal spheres suspended in a complex fluid is very different than the diffusive Brownian motion of similar spheres suspended in a purely viscous fluid (e.g simple Newtonian fluid). When suspended in complex fluids, which exhibit elasticity, the probe particles exhibit sub diffusive motion or if the elasticity becomes very significant the probe particles may become locally bound. As the microstructure slowly relaxes, it allows the particles to escape this elastic 'cage.' This motion of probe particles as a function of time can be obtained from mean squared displacement $<\Delta r^2(t)>$ of probe particles which can be obtained from the electric field autocorrelation function obtained from a Dynamic Light Scattering (DLS) experiment:

$$g^{(1)}(\tau) = \exp\left(-\frac{1}{6}q^2\Delta r^2(\tau)\right)$$

Once the mean squared displacement, $<\Delta r^2(t)>$ is obtained, it can be related through to the complex viscoelastic modulus G* and through to the elastic G' and viscous modulus G" through:

$G'(\Omega)=|G^*(\Omega)|\cos(\pi\alpha(\Omega)/2)$, $G''(\Omega)=|G^*(\Omega)|\sin(\pi\alpha(\Omega)/2)$, where $$|G^*(\omega)| \approx \frac{k_B T}{\pi a \langle \Delta r^2(1/\omega)\rangle \Gamma[1+\alpha(\omega)]}.$$

This analysis is based on two key assumptions:
The system exhibits single scattering. As the system becomes multiply scattering the analysis no longer remains valid.
The scattering is dominated by the embedded probe particles, as the whole principle is based on following the motion of the embedded probe particles.

Many complex fluids at even moderate concentrations start to contribute quite significantly to the scattered light signal. In order to ensure the domination of the scattering by probe particles, they need to be added in moderately high concentrations (but still much less than 0.5 vol %). Adding probe particles in these moderately concentrated regimes makes the system quite turbid and multiple scattering tends to become very significant.

In these types of systems, the concentration of probe particles can be raised even further to enter into the strongly multiply scattering regime, while changing the analysis from that described above to theories developed for using the multiply scattered light in the microrheological analysis. This then evolves into a technique known as Diffusing Wave Spectroscopy (DWS). An important concern for this technique is that the analysis is inherently complicated and makes interpretation of data highly challenging. The agreement of data obtained from DWS with mechanical data is in many cases quite poor and requires rescaling.

SUMMARY OF THE INVENTION

Several aspects of the invention are disclosed in this application.

Instruments according to the invention can be advantageous in that they can allow for advanced rheological characterization on very small sample volumes. They can also allow access to very high-frequency (short time) dynamics.

Instruments according to the invention may allow for improvements in viscoelasticity measurements in a variety of application areas These can include high-frequency rheological characterization of complex fluids for academic research, personal care, chemicals, and foods, where instruments according to the invention can provide an alternative to piezoelectric approaches (PAV/PRV) and DWS. Instruments according to the invention can also be used in life sciences applications, such as for advanced rheological characterization of proteins and other biopolymers in solution. In the field of chemicals and specialty chemicals, instruments according to the invention may be used for advanced rheological characterization of newly synthesized polymers or other chemicals.

Instruments according to the invention may also be used in high-throughput applications in a variety of areas, such as academic and pharmaceutical research, personal care, and chemicals.

DETAILED DESCRIPTION OF AN ILLUSTRATIVE EMBODIMENT

Figure 1:
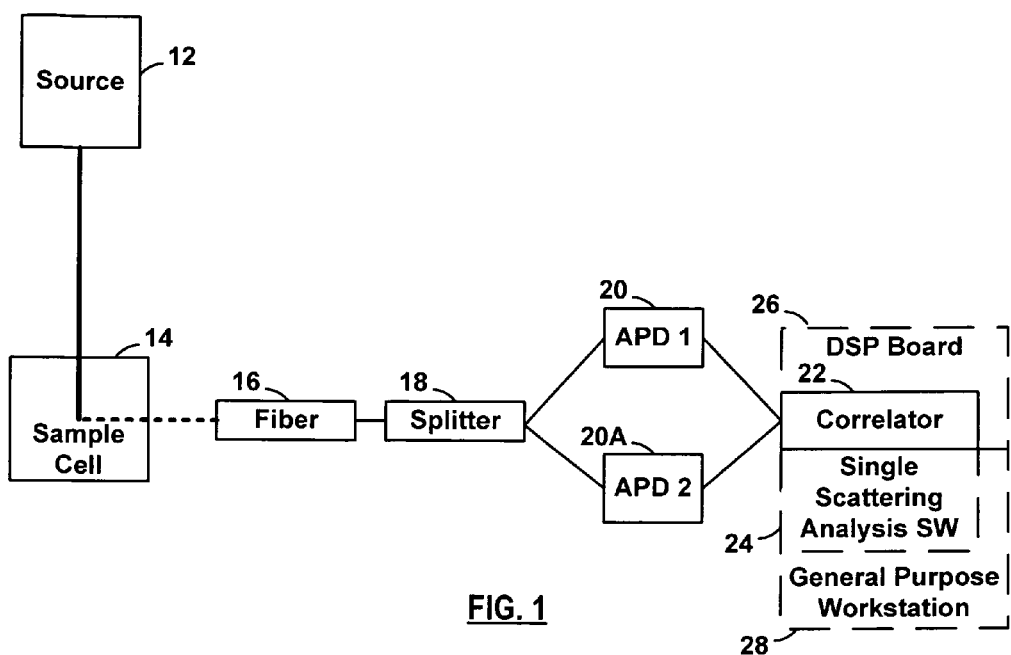
FIG. 1 is a block diagram of a microrheological fluid characteristic measurement instrument according to the invention.
Figure 2:
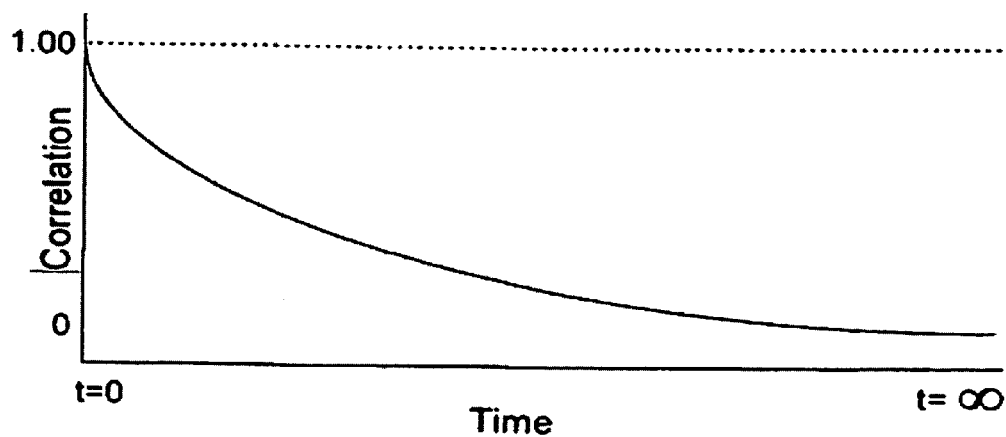
FIG. 2 is a plot of an illustrative correlation function for the instrument of FIG. 1.

Referring again to FIG. 1, in this example, the correlation operation is performed on board the instrument in a dedicated DSP board 26 and single-scattering analyses are performed using specialized software 24 running on a general-purpose workstation 28. The instrument can also use other approaches to perform these operations, such as dedicated hardware or a combination of software and dedicated hardware.

Figure 5:
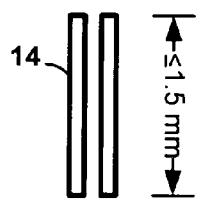
FIG. 5 is a diagrammatic illustration of a cross-section of a capillary tube that can be used as a sample cell in the instrument of FIG. 1.
Figure 6:
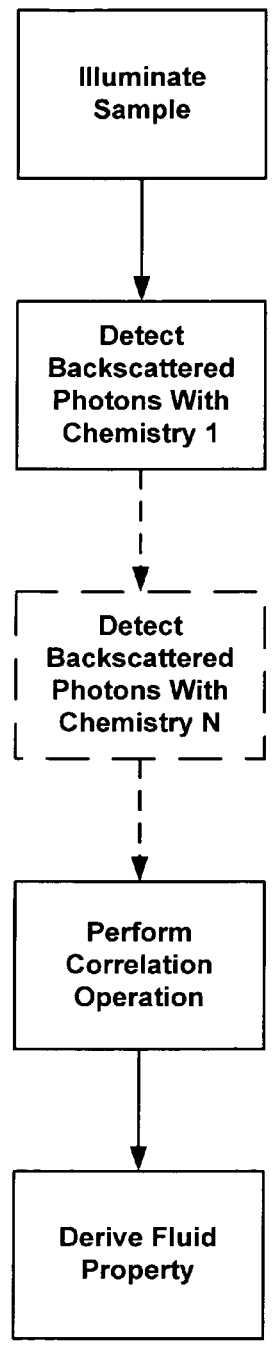
FIG. 6 is a flowchart illustrating an illustrative operation sequence according to the invention.

The sample cell 14 can be a short-path-length cell, such as a capillary tube having a diameter of 1.5 mm or less (see FIG. 5). The use of such short-path-length cells allows the instrument to minimize multiple scattering contributions to the correlation function in the transmission geometry. It is also beneficial in that it allows the instrument to make measurements based on small sample amounts, which is particularly important for biomolecules, such as proteins and small-molecule drugs, for which samples can be particularly small. This can allow the instrument to be used as part of a high-throughput screening system.

The instrument can perform forward-scattering measurements, backscatter measurements, or both. The use of backscatter detection using Non-Invasive Back-Scatter (NIBS) techniques can also help to minimize effect of multiple scattering contributions to the correlation function. This technique involves performing backscattering measurements at close to 180°, (e.g., 173°), and is described in U.S. Pat. No. 6,016,195, German patent 19725211, and Japanese patent no. 2911877, which are herein incorporated by reference. The exact NIBS detector spacing and angles will depend on a variety of factors, including the nature of the sample, the material used for the sample vessel, and the desired accuracy.

The instrument 10 can also include a fibre 16, a splitter 18, such as a 50:50 splitter, and a second detector 20A. The correlator 24 can include cross-correlation logic that allows the instrument to perform a cross-correlation between the signals from the two detectors. This correlation operation allows the instrument to more accurately extract a particle size for samples which are poor scatterers and or are small (a few nm) in size because the effect of the detector dead time, which determines the shortest autocorrelation time, will be reduced. The cross-correlation operation is also beneficial because it is less sensitive to detector noise issues, such as afterpulsing, which are uncorrelated between the detectors. And it can allow the correlator to directly determine the zero time correlation (intercept) of the correlation function, improving the calculation of the high frequency G' and G".

As discussed above, instruments according to the invention can be used as part of different kinds of high-throughput screening systems. Such systems generally include large-scale sample management systems, such as ones that are based on scanning mirrors or robotic X-Y stages. The Malvern Zetasizer APS, for example, provides off-the-shelf automated measurements of samples in industry standard 96- or 384-well plates. To detect bulk properties of the fluids, the sample vessels should have a capacity that is substantially larger than a domain size of the complex sample fluid and is sufficiently large to cause bulk scattering effects to substantially exceed surface effects for the complex fluid sample. Exact sample vessel volumes depend on a variety of factors, including the nature of the sample and desired accuracy levels.

Instruments according to the invention can be configured to allow scattered light to be detected over a range of different angles, such as from 173° to 13.5°. They can also be configured to allow measurements to be carried out in both backscattering mode or transmission mode in order to obtain an extended region of frequency response. These objectives can be accomplished in different ways, such as by allowing a single detector to move or by providing more than one detector. Measurements can also be carried out using a range of different probe sizes ranging from 30 nm to 1 um in order to extend obtained frequency and/or minimise multiple scattering by adjusting a volume of required probe particles. And measurements can be carried out using a range of different probe chemistries to minimise interactions with a complex fluid of interest.

EXAMPLE 1

In order to validate the above approach, DLS-based optical microrheology was carried out on the Zetasizer Nano (Malvern Instruments Limited) without any hardware modifications. It should be noted that the Zetasizer Nano is designed to implement the NIBS based technique. The Zetasizer Nano is described, for example in U.S. provisional application no. 61/206,688, which is herein incorporated by reference.

The system investigated was a 2M molecular weight PEO (Polyethylene Oxide) formulation at a number of different concentrations. This system was already quite turbid even at low concentrations (0.5 wt %) and was contributing significantly to the scattered light signal. In order to ensure domination of the scattering by the probe particles (700 nm nominal diameter, Polystyrene particles, Duke Scientific) they were added in relatively high concentrations, which took the system into the moderately multiply scattered regime. As the samples were visibly quite turbid, measurements would likely have been very difficult to carry out for them using traditional DLS-based microrheology.

Figure 3:
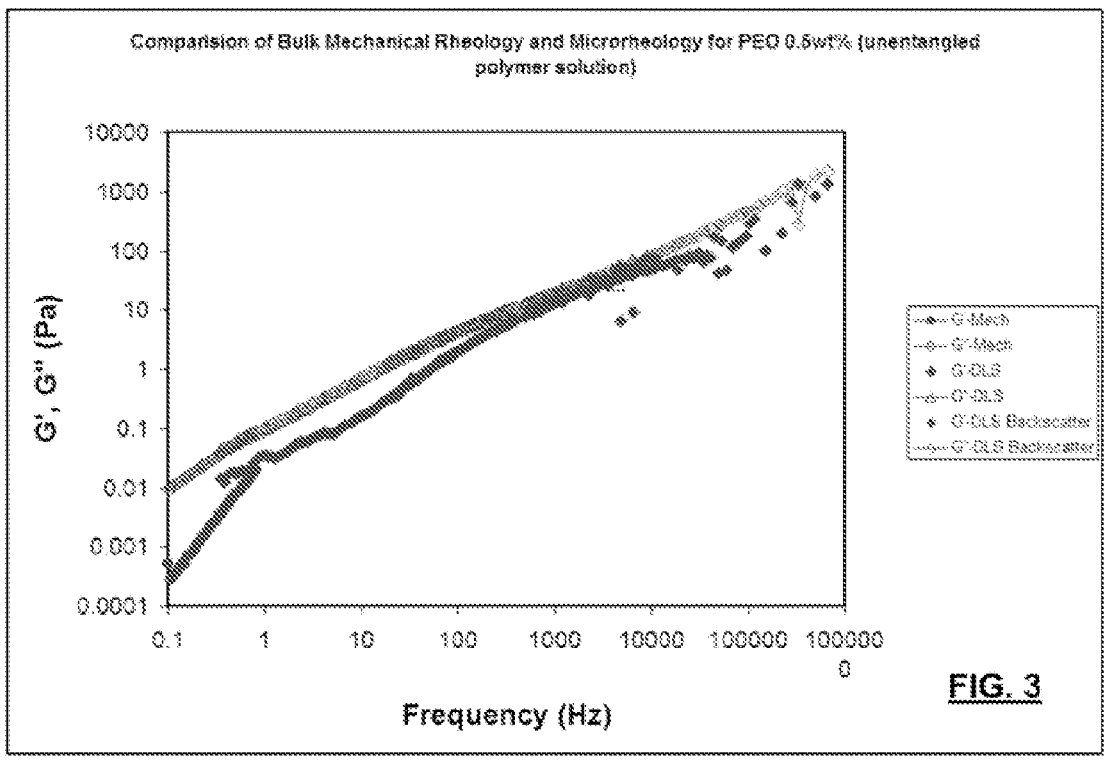
FIG. 3 is a plot of DLS-based microrheology data for a 0.5% by weight PEO solution using the instrument of FIG. 1, with mechanical rheometry results also shown for the same sample.
Figure 4:
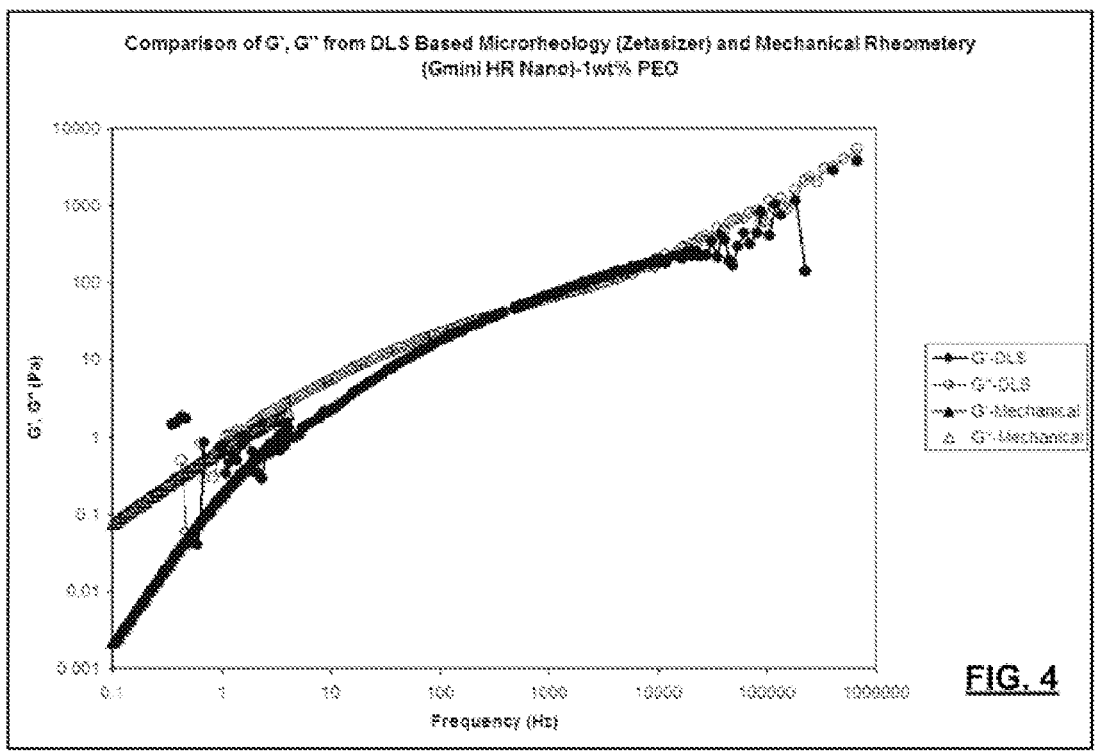
FIG. 4 is a plot of DLS-based microrheology data for a 1.0% by weight PEO solution using the instrument of FIG. 1, with mechanical rheometry results also shown for the same sample.

FIGS. 3 and 4 illustrate microrheological data obtained from the Zetasizer and comparable data for a high end rotational mechanical rheometer (Bohlin Gemini HR Nano, Malvern Instruments Limited). The data clearly illustrates very good agreement with the mechanical data at the low frequency overlap region and also illustrates the extensive frequency range over which the viscoelastic response was obtained. The DLS-based high-frequency data adequately captures the physics (Zimm and Rouse Dynamics) that is expected for this system.

In this example, the correlation operation is performed on board the instrument in a dedicated DSP board and single-scattering analyses are performed using specialized software running on a general-purpose workstation. The instrument can also use other approaches to perform these operations, such as dedicated hardware or a combination of software and dedicated hardware.

The present invention has now been described in connection with a number of specific embodiments thereof. However, numerous modifications which are contemplated as falling within the scope of the present invention should now be apparent to those skilled in the art. Therefore, it is intended that the scope of the present invention be limited only by the scope of the claims appended hereto. In addition, the order of presentation of the claims should not be construed to limit the scope of any particular term in the claims.

The invention claimed is:

1. A fluid characterization measuring instrument, comprising:
   a sample vessel for a bulk complex sample fluid having a capacity that is substantially larger than a domain size of the complex sample fluid and that is sufficiently large to cause bulk scattering effects to substantially exceed surface effects for the complex fluid sample,
   a coherent light source positioned to illuminate the bulk complex sample fluid in the sample vessel,
   a first fibre having a first end positioned to receive backscattered light from the sample after it has interacted with the sample, wherein the first fibre is positioned close enough to an optical axis of the coherent light source and to the sample vessel to substantially decrease a contribution of multiply scattered light in the backscattered light,
   a first photon-counting detector positioned to receive the backscattered light from a second end of the fibre,
   correlation logic responsive to the first photon-counting detector, and
   single-scattering fluid property analysis logic responsive to the correlation logic and operative to derive at least one fluid property for the sample fluid.

2. The instrument of claim 1 wherein the instrument is constructed and adapted to allow the photon detector to allow scattered light to be detected over a range of different angles ranging from 173° to 13.5°.

3. The instrument of claim 1 wherein the instrument is constructed and adapted to allow the first photon-counting detector to be further responsive to forward scattered light.

4. The instrument of claim 1 wherein the center of the scattering volume can be selectively positioned substantially at the surface of the sample fluid.

5. A fluid characterization measuring instrument, comprising:
   a sample vessel for a sample fluid,
   a coherent light source positioned to illuminate the sample fluid in the sample vessel,
   a splitter having an input responsive to light scattered by the sample and having first and second outputs,
   a first photon-counting detector positioned to receive a first portion of the scattered light from a first output of the splitter,
   a second photon-counting detector positioned to receive a second portion of the scattered light from a second output of the splitter,
   cross-correlation logic responsive to the first photon-counting detector and to the second photon-counting detector, and
   single-scattering fluid property analysis logic responsive to the correlation logic and operative to derive at least one fluid property for the sample fluid.

6. A fluid characterization measuring instrument, comprising:
   a sample vessel for a bulk complex sample fluid having a capacity that is substantially larger than a domain size of the complex sample fluid and that is sufficiently large to cause bulk scattering effects to substantially exceed surface effects, and wherein the sample vessel has an optical path length of about 1.5 mm or less,
   a coherent light source positioned to illuminate the sample fluid in the sample vessel through the optical path length,
   a first photon-counting detector positioned to receive light scattered by the sample,
   correlation logic responsive to the first photon-counting detector, and
   single-scattering fluid property analysis logic responsive to the correlation logic and operative to derive at least one fluid property for the sample fluid.

7. A microrheological measuring method, including the steps of:
   illuminating a sample of a complex fluid with coherent light, wherein a volume of the sample of the complex fluid is substantially larger than a domain size of the complex sample fluid and is sufficiently large to cause bulk scattering effects to substantially exceed surface effects for the complex fluid sample,
   detecting backscattered photons from the sample from a position that is close enough to an optical axis of the coherent light and to the sample to substantially decrease a contribution of multiply scattered light arising from scattering of light from the coherent light in the backscattered light,
   performing a correlation operation on a detection signal representative of the detected backscattered photons, and
   deriving at least one fluid property from results of the correlation operations for the sample fluid based on single-scattering analysis.

8. The method of claim 7 wherein the correlation operation is an autocorrelation operation.

9. The method of claim 7 wherein scattered light is detected over a range of different angles ranging from 173° to 13.5° and wherein the steps of performing a correlation operation and deriving are performed for the light detected over a range of angles.

10. The method of claim 7 wherein steps of detecting are carried out in both backscattering mode and forward transmission mode in order to obtain an extended region of frequency response.

11. The method of claim 7 wherein steps of detecting are carried out using a range of different probe sizes ranging from 30 nm to 1 um in order to extend obtained frequency and/or minimise multiple scattering by adjusting volume of required probe particles.

12. The method of claim 7 wherein steps of detecting are carried out using a range of different probe chemistries to minimise interactions with the complex fluid of interest.

13. A viscoelecicity measuring method, including the steps of:
   illuminating a sample fluid with coherent light,
   splitting scattered light received from the sample into first and second portions,
   detecting photons from the first portion of the scattered light,
   detecting photons from the second portion of the scattered light, performing a cross-correlation operation between a first detection signal representative of the backscattered photons in the first portion and a second detection signal representative of the backscattered photons in the second portion, and deriving at least one fluid property from results of the correlation operation for the sample fluid based on single-scattering analysis.

14. A viscoelecicity measuring method, including the steps of:

illuminating a sample of a complex fluid with coherent light through an optical path length of about 1.5 mm or less, wherein a volume of the sample of the complex fluid is substantially larger than a domain size of the complex sample fluid and is sufficiently large to cause bulk scattering effects to substantially exceed surface effects for the complex fluid sample, detecting photons from light scattered from the sample, performing a correlation operation on a detection signal representative of the scattered photons, and deriving at least one fluid property from results of the correlation operation for the sample fluid based on single-scattering analysis.

15. A microrheological measuring method, including the steps of:

embedding probe particles into a complex fluid sample, illuminating the complex fluid sample with coherent light, detecting backscattered photons from the scattering of the coherent light by the probe particles in the complex fluid sample from a position that is close enough to an optical axis of the coherent light and to the sample to substantially decrease a contribution of multiply scattered light in the detected backscattered photons, performing a correlation operation on a detection signal representative of the detected backscattered photons, and deriving at least one rheological property of the complex sample fluid from results of the correlation operation.

16. The instrument of claim 7 wherein the sample vessel is a capillary tube.

17. The method of claim 15 further including detecting forward scattered photons from the scattering of the coherent light by the probe particles in the complex fluid sample in order to obtain an extended region of frequency response.

18. The method of claim 15 wherein the correlation operation is an autocorrelation operation.

19. A microrheological measuring method, including the steps of:

embedding probe particles into a complex fluid sample, illuminating the complex fluid sample with coherent light, detecting forward-scattered photons from the scattering of the coherent light by the probe particles in the complex fluid sample from a position that is close enough to an optical axis of the coherent light and to the sample to substantially decrease a contribution of multiply scattered light in the detected forward-scattered photons, performing a correlation operation on a detection signal representative of the detected forward-scattered photons, and deriving at least one rheological property of the complex sample fluid from results of the correlation operation.

20. The method of claim 19 wherein the correlation operation is an autocorrelation operation.

21. A fluid characterization measuring instrument, comprising:

a sample vessel for a bulk complex sample fluid having a capacity that is substantially larger than a domain size of the complex sample fluid and that is sufficiently large to cause bulk scattering effects to substantially exceed surface effects for the complex fluid sample, a coherent light source positioned to illuminate the bulk complex sample fluid in the sample vessel, a first photon-counting detector positioned to receive scattered light from the sample after it has interacted with the sample, wherein the detector receives light from a position close enough to an optical axis of the coherent light source and to the sample vessel to substantially decrease a contribution of multiply scattered light in the scattered light, correlation logic responsive to the first photon-counting detector, and single-scattering fluid property analysis logic responsive to the correlation logic and operative to derive at least one fluid property for the sample fluid.

22. The instrument of claim 21 wherein the correlation logic includes an autocorrelator.

23. The instrument of claim 21 wherein the detector is positioned to receive the scattered light through an optical fibre.

24. The instrument of claim 21 wherein the detector is positioned to receive backscattered light.

25. The instrument of claim 21 wherein the detector is positioned to receive forward scattered light.

26. The instrument of claim 21 wherein an optical path length through which the sample is illuminated is sufficiently short to substantially decrease a contribution of multiply scattered light in the scattered light.

* * * * *